United States Patent
Atiba

(10) Patent No.: US 11,980,627 B2
(45) Date of Patent: *May 14, 2024

(54) TRIPLE PHARMACEUTICAL COMPOSITION FOR PROTEINACEOUS INFECTION

(71) Applicant: Joshua O. Atiba, Watsonville, CA (US)

(72) Inventor: Joshua O. Atiba, Watsonville, CA (US)

(*) Notice: Subject to any disclaimer, the term of this patent is extended or adjusted under 35 U.S.C. 154(b) by 77 days.

This patent is subject to a terminal disclaimer.

(21) Appl. No.: 17/618,871

(22) PCT Filed: Jun. 15, 2020

(86) PCT No.: PCT/US2020/037787
§ 371 (c)(1),
(2) Date: Dec. 13, 2021

(87) PCT Pub. No.: WO2020/252475
PCT Pub. Date: Dec. 17, 2020

(65) Prior Publication Data
US 2022/0305036 A1   Sep. 29, 2022

Related U.S. Application Data

(63) Continuation-in-part of application No. 16/504,723, filed on Jul. 8, 2019, now abandoned.

(60) Provisional application No. 62/861,855, filed on Jun. 14, 2019.

(51) Int. Cl.
| | | |
|---|---|---|
| *A61K 31/65* | (2006.01) | |
| *A61K 31/40* | (2006.01) | |
| *A61K 31/436* | (2006.01) | |

(52) U.S. Cl.
CPC .............. *A61K 31/65* (2013.01); *A61K 31/40* (2013.01); *A61K 31/436* (2013.01)

(58) Field of Classification Search
CPC ...... A61K 31/40; A61K 31/436; A61K 31/65; A61K 2300/00; A61P 31/04; A61P 37/06
See application file for complete search history.

(56) References Cited

U.S. PATENT DOCUMENTS

| | | |
|---|---|---|
| 10,350,226 B1 | 7/2019 | Atiba |
| 2001/0014670 A1* | 8/2001 | Balin ............ A61K 31/7052 |
| | | 514/29 |
| 2004/0014670 A1 | 1/2004 | Kodera et al. |
| 2004/0127471 A1* | 7/2004 | Reisberg ............ A61K 31/19 |
| | | 514/557 |
| 2005/0271717 A1* | 12/2005 | Berchielli ............ A61P 3/10 |
| | | 424/464 |
| 2016/0045520 A1 | 2/2016 | De Silvestri et al. |
| 2016/0354730 A1 | 12/2016 | Reid |
| 2017/0333469 A1 | 11/2017 | Vogt et al. |

FOREIGN PATENT DOCUMENTS

WO   WO-2018108991 A2 *   6/2018   .......... A61K 31/166

OTHER PUBLICATIONS

Bagherpour, Multiple Sclerosis and Related Disorders, 26, 2018, 40-45 (Year: 2018).*
Luccarini, Experimental Neurology, 211, May 1, 2008, p. 214-226 (Year: 2008).*
ISA/US, International Search Report and Written Opinion for PCT Application No. PCT/US2020/037787, mail date Sep. 9, 2020. 6 pages.

* cited by examiner

*Primary Examiner* — Umamaheswari Ramachandran
(74) *Attorney, Agent, or Firm* — SoCal IP Law Group LLP; Steven C. Sereboff; Brian S. Tamsut

(57) ABSTRACT

There are disclosed therapies and preventions of prion protein complex infections. The transcription of the amyloid precursor protein gene and PrP gene and the RNA transcript are the rate-limiting steps and are most susceptible for blockage and control of the process of amyloid protein formation and $PrP^{sc}$ formation. Thus, therapies and prevention regimes for prion protein complex infections interrupt this process at the level of DNA transcription to RNA, RNA transport to the mitochondrion for protein synthesis and deposition in the cerebral cortex neurons.

2 Claims, 5 Drawing Sheets

The Witch's Brew

TRIPLE PHARMACEUTICAL COMPOSITION FOR PROTEINACEOUS INFECTION

This patent claims priority from International PCT Patent Application No. PCT/US2020/037787 filed Jun. 15, 2020 entitled, "TRIPLE PHARMACEUTICAL COMPOSITION FOR PROTEINACEOUS INFECTION", which claims priority to U.S. application Ser. No. 16/504,723 filed Jul. 8, 2019 entitled, "Therapy and Prevention of Prion Protein Complex Infections," and U.S. provisional application 62/861,855 filed Jun. 14, 2019 entitled "TRIPLE PHARMACEUTICAL COMPOSITION FOR PROTEINACEOUS INFECTION" all of which are incorporated herein by reference in their entirety.

BACKGROUND

Field

This disclosure relates to Alzheimer's disease (AD) therapy.

Description of the Related Art

AD is commonly believed to be a localized brain disease. AD with neurological disease is the third leading cause of death in the United States after cardiovascular diseases and cancer. AD normally follows a sequence comprised of neuro-inflammation, amyloid and tau proteopathy, accumulative storage disease, neurotoxicity and neurodamage, loss of function (i.e., activities of daily living (ADL) and cognitive skills), and finally death. AD deaths are due to the futility and loss of will to live in these patients who have been depersonalized and lost their appetite for food and liquids, coupled with the failure to thrive leading to premature death usually within five to ten years of diagnosis of AD.

There are four main prevailing theories about the causation of AD: (a) a cholinergic hypothesis, (b) an amyloid protein deposition hypothesis, (c) a tau protein deposition hypothesis, and (d) a neurovascular hypothesis. Presently there is no effective treatment capable of modifying the progression of Alzheimer's disease, or preventing its onset. Currently available therapies only act on symptomatic improvement, while the development of therapies capable of blocking or delaying the disease progression remains a challenging unmet need.

According to the cholinergic hypothesis, degeneration of cholinergic neurons in the basal forebrain and the associated loss of cholinergic neurotransmission in the cerebral cortex and other areas contributed significantly to the deterioration in cognitive function seen in patients with Alzheimer's disease.

Under the amyloid protein deposition hypothesis, the formation of amyloid plaques and neurofibrillary tangles are thought to contribute to the degradation of the neurons (nerve cells) in the brain and the subsequent symptoms of Alzheimer's disease. Amyloid proteins are a large group of proteins of which sixty different types have been described. Thirty-six amyloid proteins have been associated with human disease. Amyloid protein was first seen and described by Rudolf Virchow who thought it was a starchy substance hence the name amyloid related to starch or "amylin" in Latin. It was next thought to be a fatty substance, but later found to be a protein substance. Since the introduction of elegant protein chemistry, mass spectrometry, and x-ray crystallography, amyloid proteins have been better characterized and identified in various human diseases and conditions.

Amyloid protein disease was once classified as primary or secondary amyloidosis. Primary disease was recognized as familial disease with synthesis and deposition of the protein in organs such as the heart, kidney, skin, tongue, fat tissue, and rectum. In secondary disease, amyloid protein deposition was recognized as secondary to a chronic suppurative condition such as tuberculosis or other uncontrolled bacterial abscess which is common in developing and underdeveloped nations of the world. Similarly, chronic inflammatory conditions, such as rheumatoid arthritis and renal dialysis, lead to secondary and reactive amyloid protein deposition.

Amyloid precursor protein (APP), which is encoded in chromosome 21, has a role in AD. APP is a trans-membrane protein that penetrates through the neuron's membrane, and is critical for neuron growth, survival, and post-injury repair. Thus, loss of a neuron's APP may affect physiological and pathophysiological deficits that contribute to dementia. Clinical data from individuals with Down syndrome (i.e., trisomy 21) shows that they develop AD earlier in their 30s to 40s, since the gene for APP is in chromosome 21, and they are saddled with three copies. This is akin to patients with inflammatory bowel disease (IBD) who develop colon cancer in their 30-40s compared to normal population who develop it in their 50s to 80s. APP is copied and used to synthesize amyloid protein.

Amyloid beta (AB) is the specific amyloid protein implicated in AD. Amyloid plaques are made up of small peptides, 39-43 amino acids in length. Amyloid beta is produced from the sequential cleavage of APP by beta-site amyloid precursor protein-cleaving enzyme 1 (BACE-1) followed by gamma-secretase. In AD, gamma secretase and beta secretase act together in a proteolytic catabolic reaction, cleaving a smaller fragment of APP. These protein catabolism fragments then form fibrils of amyloid beta, which further form clumps deposited outside the neurons known as senile plaques.

Because Aβ accumulates excessively in AD, there is a logical inference that its precursor, APP, would be elevated as well. However, a study has shown that neuronal cell bodies contain less APP as a function of their proximity to amyloid plaques. It has been theorized that this APP deficit near AB plaques results from a decline in production of APP which normally rises in response to stress.

Several BACE-1 inhibitors, BACE-2 inhibitors and humanized monoclonal antibodies to soluble amyloid protein have been in clinical trials in AD. These trials failed to deliver on the promise of being disease modifying drug (DMD) agents (i.e., they change the underlying pathology of the disease) in AD. Similarly, vaccines have been tried to clear amyloid protein plaques in AD all to no avail. In light of the failure of clinical trials using BACE inhibitors, and the failure of amyloid immunotherapy with intravenous Solanezumab, the amyloid protein deposition theory has been called into question.

The tau protein deposition hypothesis proposes that tau protein abnormalities initiate the disease cascade. In this model, hyperphosphorylated tau begins to pair with other threads of tau. Eventually, they form neurofibrillary tangles inside nerve cell bodies When this occurs, the microtubules disintegrate, destroying the structure of the cell's cytoskeleton which collapses the neuron's transport system. This may result first in malfunctions in biochemical communication between neurons and later in the death of the cells.

The neurovascular hypothesis claims that a substantial amount of Aβ peptide in the brain of Alzheimer's disease patients is originated in the systemic circulation. According to this theory, poor functioning of the blood-brain barrier (BBB) is involved. One side effect of this poor function is production of amyloid and tau hyper-phosphorylation.

Prion (PrP) is a protein which arises from misfolding of a normal protein. The two forms of prion are designated as $PrP^c$, which is a normally folded protein, and $PrP^{sc}$, a misfolded form which gives rise to the disease. The two forms do not differ in their amino acid sequence, however the pathogenic $PrP^{sc}$ isoform differs from the normal $PrP^c$ form in its secondary and tertiary structure. The $PrP^{sc}$ isoform is more enriched in beta sheets, while the normal $PrP^c$ form is enriched in alpha helices. The differences in conformation allow $PrP^{sc}$ to aggregate with amyloidβ fibrils and be extremely resistant to protein degradation by enzymes or by other chemical, radiation and physical means. The normal form, on the other hand, is susceptible to complete proteolysis and soluble in non-denaturing detergents. It has been suggested that pre-existing or acquired $PrP^{sc}$ can promote the conversion of $PrP^c$ into $PrP^{sc}$, which goes on to convert other $PrP^c$. This initiates a chain reaction that allows for its rapid propagation, resulting in the pathogenesis of prion diseases. $PrP^c$ protein is one of several cellular receptors of soluble amyloid beta (Aβ) oligomers.

The highly conserved genetic sequence of PrP yet lack of characterized function has puzzled researchers for years. Researchers have tried to link PrP and Aβ to other diseases but have been unsuccessful. Some research has tried to hypothesize that because Aß is a type of protein plaque it must also be linked with heart disease. However, some heart disease does not contain Aß plaques, and a significant amount of AD patients do not have heart disease. Studies treating heart disease with antibiotics have proven unsuccessful. Not only have these studies focused on treatment of bacteria rather than inflammation or plaque buildup, but these studies conclude that treatment with antibiotics will likely have no beneficial effects. One study summarized the field's current state as, "[t]he clinical trial data to date have not provided adequate support for the clinical use of antibiotics in primary or secondary prevention of coronary heart disease." [Anderson et al., 2004].

Apolipoprotein E (ApoE) transports lipids, fat-soluble vitamins, and cholesterol into the lymph system and then into the blood which is the principal cholesterol carrier in the brain. The gene for ApoE is mapped to chromosome 19. ApoE is polymorphic with three major alleles: ApoE-ε2, ApoE-ε3, and ApoE-ε4. Although these allelic forms differ from each other by only one or two amino acids at positions, these differences alter ApoE structure and function. These differences have physiological consequences. ApoE-ε4 has an allele frequency of approximately 14 percent and has been heavily implicated in late onset Alzheimer's disease (LOAD).

Research for a cure to AD also yields no promising results. Researchers have tried the gambit of treatment, from designer drugs, to custom proteins, to antibiotics, but none have been successful. Numerous studies have suggested that a treatment of antibiotics could not cure AD. In 2013 researchers conducting a study on doxycycline and rifampin stated, "Conclusion: twelve months' treatment with doxycycline or rifampin, alone or in combination, has no beneficial effects on cognition or function in AD" [Molloy et al., 2012].

Another study looking at possible treatments for AD characterized the Molloy study, "but there were no differences between treatment and placebo groups at 3 and 12 months. However, no beneficial effects on cognition or functioning were detected when doxycycline was used alone or in combination with rifampin" [Appleby et al., 2013].

Other studies in which AD patients are treated with antibiotics show both treated and untreated groups declining in cognitive function. [Boyles 2003]. Researchers of AD have been skeptical of antibiotic regimens as a treatment for AD, one researcher remarking, "[w]e don't propose that a long-term course of antibiotics is going to be a treatment—that's just absurd for a whole number of reasons . . ." [Minter 2016].

Researchers are also skeptical that other drugs can treat AD. The National Institute on Aging has stated although NSAIDs mainly operate by targeting inflammation, to date, there have been no clinical trials in which patients of AD have benefited from the actual use of NSAIDs. NSAIDs have been considered a bad candidate for AD for a number of reasons. For one, AD often occurs in elderly patients, and elderly patients generally have weaker hearts. In fact, a study to check if NSAIDs could be used to fight AD had to be stopped because there were concerns over the participants' cardiovascular health. [Terrie, 2009]. Acetaminophen and aspirin were not found to have beneficial effects on AD in a study. [Szekely et al, 2008]. In another study, Naproxen and Celecoxib did not improve cognitive function in patients with AD [Martin et al, 2007].

Against this background of prion protein complex infections, we turn to several drugs which have not been proposed for therapeutic application toward prion protein complex infections. For example, although genetically engineered antibodies have been tried, antibiotics have not been considered as possible therapies for prion protein complex infections. Another class not previously considered are immunosuppressants.

The tetracyclines are a very old group of bacteriostatic antibiotics consisting of tetracycline, doxycycline and minocycline. They act by inhibiting protein synthesis in bacterial and protozoa cells and in eukaryotic organism mitochondrion, thereby inhibiting the binding of aminoacyl-tRNA to the mRNA ribosome complex. They do so mainly by binding to the 30S ribosomal subunit in the mRNA translation complex. In addition to inhibiting protein synthesis, these drugs are anti-inflammatory, are lipid soluble, and have high central nervous system concentration.

Sirolimus, also known as rapamycin, is a macrolide compound marketed under the trade name Rapamune® by Pfizer. There are numerous rapamycin derivatives (rapalogs) that function as mTOR inhibitors. New rapalogs continue to be researched and developed every day. Sirolimus has immunosuppressant effects in humans and is used in preventing the rejection of kidney transplants. It inhibits activation of T cells and B cells by reducing their sensitivity to interleukin-2 (IL-2) through mTOR inhibition. By its effect on B cells it prevents the humoral immune system from synthesizing humoral antibodies to the renal graft. Sirolimus and its rapalogs increase autophagy and mitophagy.

DETAILED DESCRIPTION

AD is not a localized brain disease. AD is a prion protein complex infection, and a systemic disease involving both the body and the peripheral circulation and B-cells. AD includes a localized reaction in the neocortex. Indeed, proof of this is the fact that AD can be diagnosed in saliva by testing for Aβ$_{42}$ level (with ELISA test), blood Aβ$_{42/40}$ ratio, and cerebrospinal Aβ$_{42}$ level. Additionally, AD can be initiated by inflammation of the brain caused by other diseases such as Parkinson's Disease and Chronic traumatic encephalopathy (CTE) from repeated brain trauma such as in boxers and footballers.

Amyloid beta protein deposition seen in AD is secondary to a chronic neuro-inflammatory condition in the acetylcholine discharging neurons of the cerebral cortex. This amyloid protein deposition starts ten to fifteen years prior to the clinical diagnosis of AD in the patient and continues until the patient dies. The transcription of the APP gene and the RNA transcript are the rate-limiting steps and are most susceptible for blockage and control of the process of amyloid protein formation. Thus, there is described or proposed herein a cure for AD based upon interruption of this process at the level of DNA transcription to transcript RNA (tRNA), messenger RNA, (cmRNA), RNA transport to the mitochondrion for protein synthesis and deposition in the cerebral cortex neurons. This is the main thrust of our effort in introducing the first DMDs in AD.

This neuroinflammation in the neocortex is concomitant with localized secretion of amyloid beta to the acetylcholine secreting memory nerve fibers, and the secretion of cellular prion protein (PrP$^c$) peptides and tau protein peptides. Because of the neurotoxicity of the amyloid protein oligomers there is the misfolding of the PrP$^c$ peptides converting them from an alpha helical structure to a beta helical structure (i.e., PrP$^{sC}$). The PrP$^{sc}$ beta helical structure interacts with Aβ fibrils and starts laying down sheets of Aβ fibrils which are neurotoxic and lead to neurotoxicity and nerve fiber and nerve cell death creating the pathognomonic amyloid plaques and the tau protein tangles.

Figure 1:
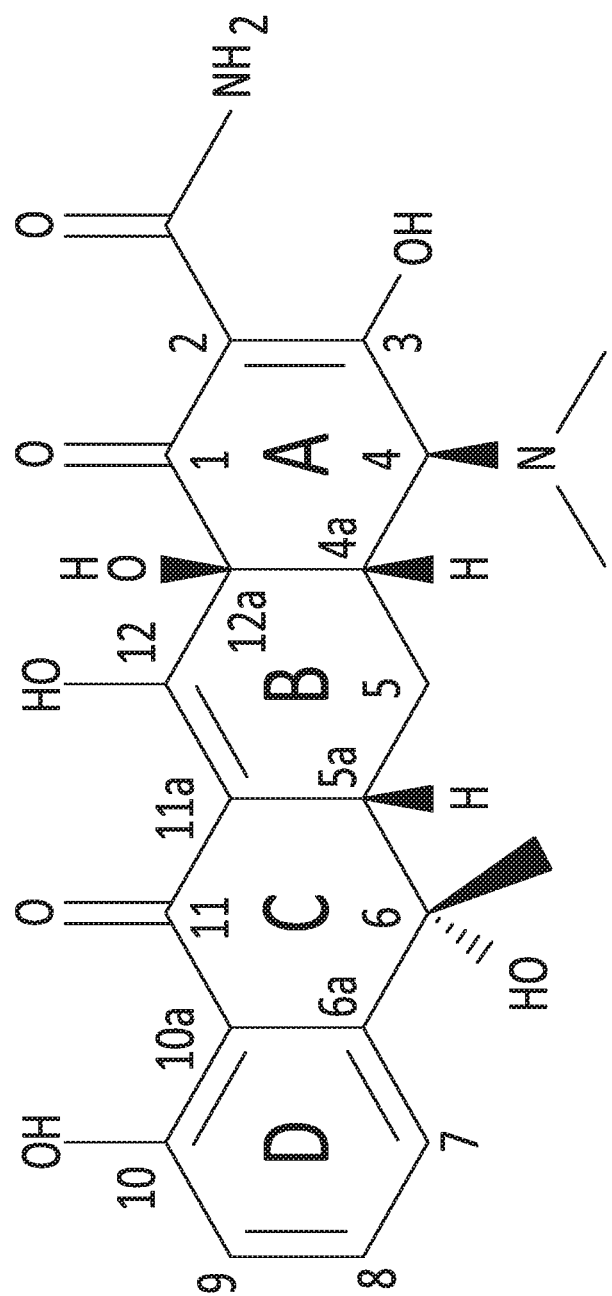
FIG. 1 is a skeletal formula of tetracycline with atoms and four rings numbered and labeled.
Figure 2:
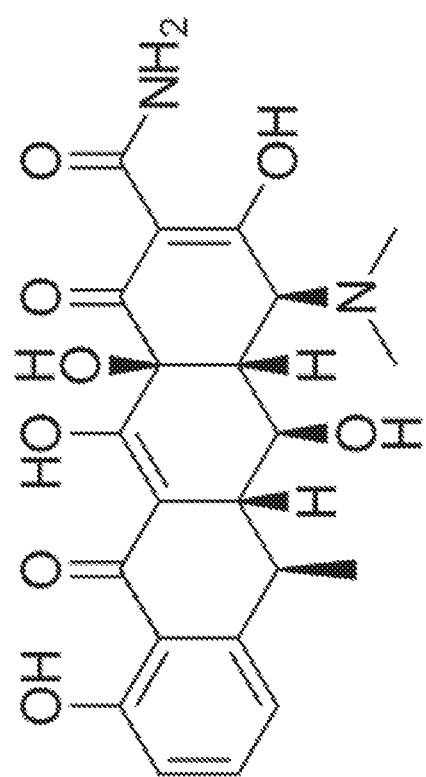
FIG. 2 is a formula for doxycycline.
Figure 3:
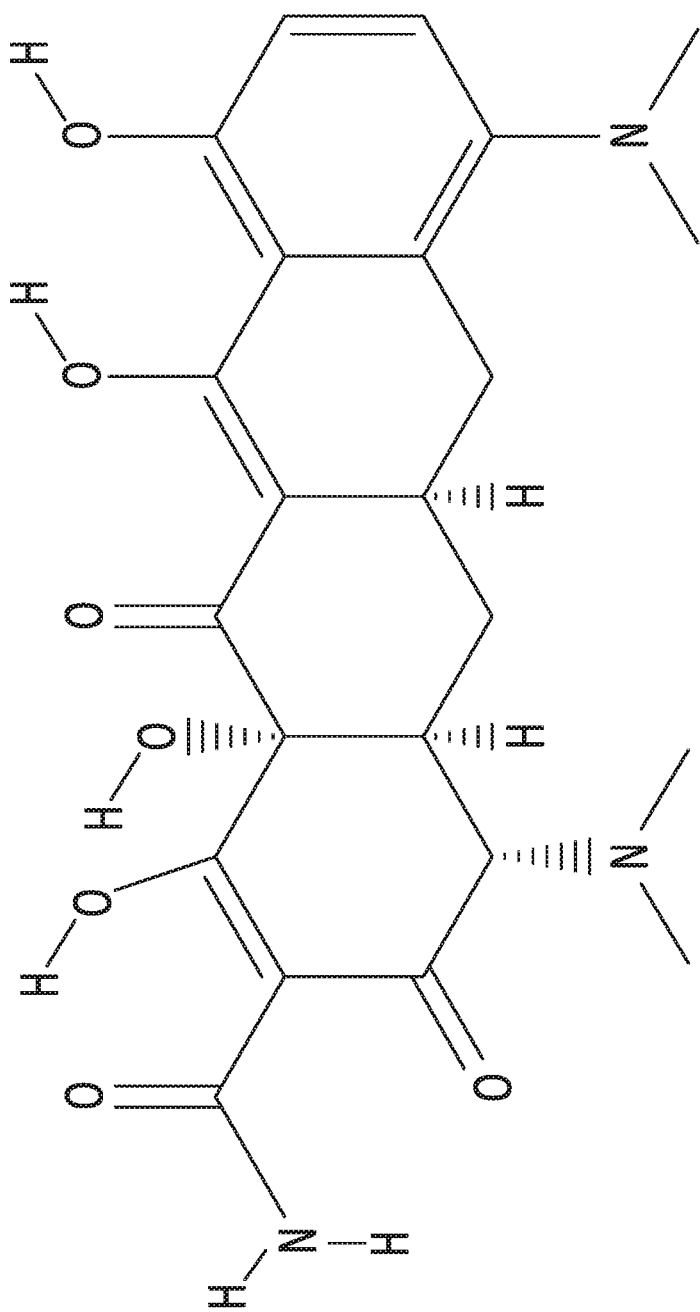
FIG. 3 is a formula for minocycline.
Figure 4:
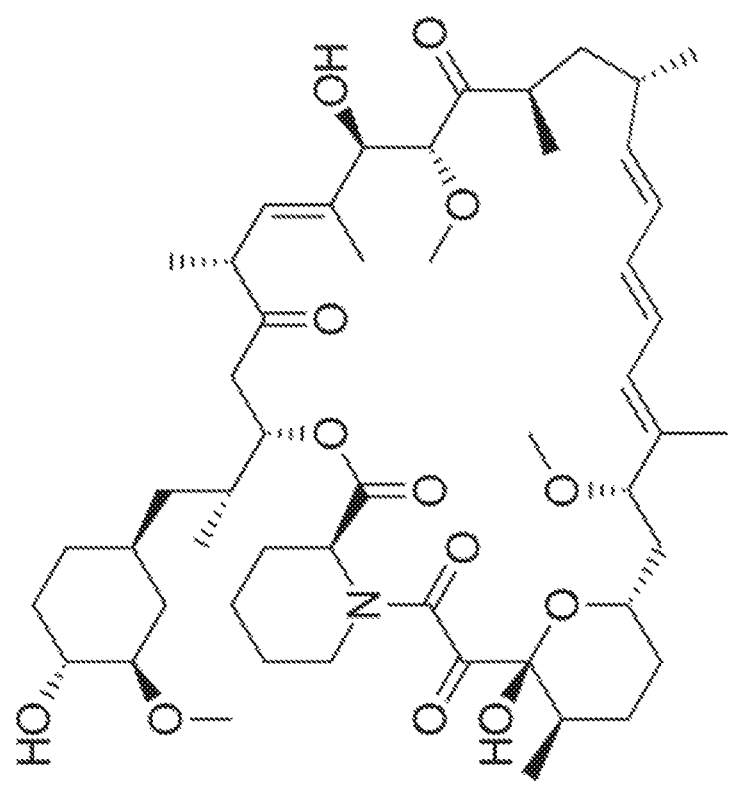
FIG. 4 is a formula for sirolimus.
Figure 5:
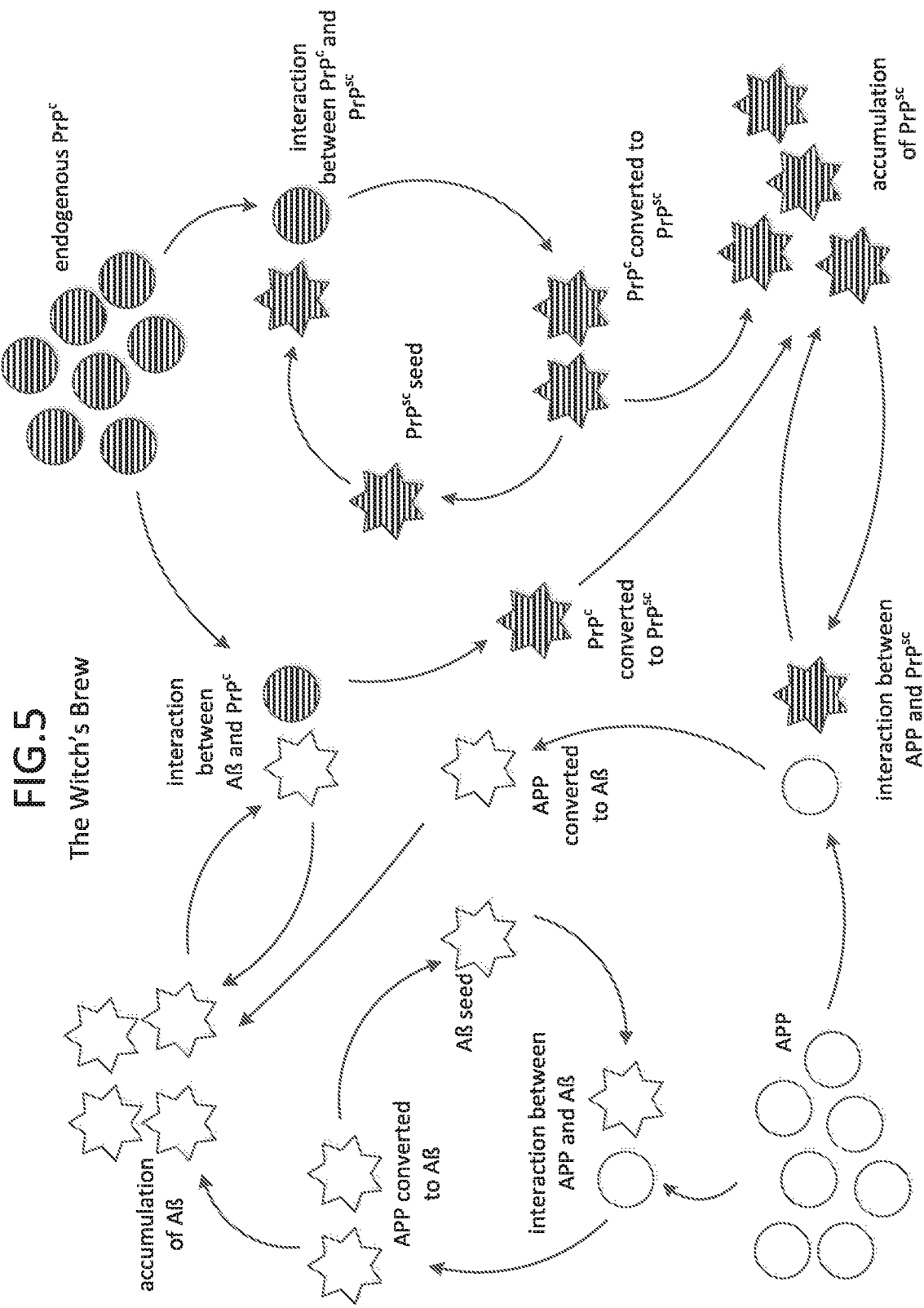
FIG. 5 is a conceptual diagram showing the basis for exponential growth of the presence of Aβ and PrP$^{sc}$.

FIG. 5 demonstrates the basis for exponential growth of the presence of AB and PrP$^{sc}$ in AD. As shown in FIG. 5, when PrP$^{sc}$ is applied to PrP$^c$, the PrP$^c$ misfolds into PrP$^{sc}$. The same behavior arises with APP and Aβ:Aβ is a seed for producing more Aβ from APP. However, these two cycles are not independent. They are interdependent. That is, Aβ seeds conversion of PrP$^c$ into PrP$^{sc}$, and PrP$^{sc}$ seeds production of Aβ from APP. Thus, this witch's brew of Aβ and PrP$^{sc}$ at the heart of prion protein complex in amyloid plaques characteristic of AD leads to a cycle of death which cannot be stopped by a therapy which only interferes with misfolding of PrP$^c$ into PrP$^{sc}$, or only interferes with production of Aβ from APP. The therapy described herein addresses both types of misfolding and generation of one precursor protein (or oligopeptides).

AD may be treated and prevented through two treatment forms. Amyloid beta protein, present in the blood, diffuses into the cerebrospinal fluid which washes over the brain and the neocortex. This creates a secondary neocortical reaction with the laying of sheets of amyloid beta fibrils, leading to the death and destruction of memory cells and creating amyloid plaques and neurofibrillary tau protein tangles. One treatment form uses an immunosuppressant to address the systemic humoral B cell reaction and prion protein transcription, translation and synthesis. The other treatment form uses an antibiotic to address synthesis of amyloid beta protein. Benefits are obtained by combining the treatment forms.

AD arises from a complex of rogue prion proteins—a witch's brew. This rogue prion protein complex consists of Aβ fibrils and prion receptor protein (PRP)β(PrP$^{sc}$) fibrils. The body's natural reaction to the rogue prion protein complex is a self-defense mechanism that itself harms tissue. These defense mechanisms take the form of a self-assembling Pacman which attacks and eats the rogue prion protein complex. Injury to the corresponding tissue is the culprit in the pathogenesis of AD and other prion protein complex infections.

The systemic disease component of AD may be treated with an immunosuppressant such as sirolimus. Sirolimus, by its effect on B cells, impairs the humoral immune system from synthesizing humoral antibodies and APP. This abrogates the systemic component of the AD pathogenesis. Currently sirolimus is only prescribed to patients that undergo transplants, and certain cancers. There is no indication for combining sirolimus with a tetracycline. Sirolimus also inhibits antibody formation and abrogates synthesis of amyloid beta protein by plasma cells and B cells in general. It also suppresses the innate immune system and the cytokines produced by microglia and macrophages such as TNFα, IL-1β, IL-6, and gamma interferon.

The central nervous system (CNS) localized effects of AD may be treated with antibiotics such as tetracyclines. Tetracyclines block protein synthesis by their effects on transcription, translation, and binding to the ribosomal protein complexes. The tetracycline compounds can deal with the CNS/neocortical component of the AD pathogenesis by inhibiting the transcription of the APP gene on chromosome 21 and the transcription of the PrP gene on chromosome 20. Additionally, the tetracyclines block translation of the gene and protein synthesis by binding to the 30S and 50S subunits of the ribosomal protein complex.

The double action through treatment of both the systemic disease component and the CNS-localized effects leads to hindering or abolition of the effect of the rogue prion protein complex in AD. By inhibiting the transcription and blocking the synthesis of amyloid protein in AD patients, we stop further amyloid protein deposition in the cerebral cortex and the subsequent neurotoxicity and neuronal damage and loss of memory and function. Patients accordingly regain function and are able to participate in their activities of daily living and interactions with family members. Similarly, by blocking the transcription and synthesis of PrP$^{sc}$, the second part of the rogue prion protein complex is disrupted.

AD patients may be characterized as three types. In Type I, the patient has Down's Syndrome, and this is approximately 0.001% of all AD cases. In Type I patients, AD manifests at about 30-40 years of age. Its genetic marker is Trisomy 21. In Type II, the patient has early onset Alzheimer's disease (EOAD), and this is approximately 1-5% of all AD cases. In Type II patients, AD manifests at about 50-60 years of age. Its genetic marker is PSEN1 and PSEN2 on Chromosome 14 and 1 respectively. In Type III, the patient has late onset Alzheimer's disease (LOAD), and this is approximately 95% of all AD cases. In Type III patients, AD manifests at about 65-90 years of age. Two-thirds of patients with Type III are APOE ε4 positive and APOE ε4 is located on chromosome 19. Type III patients may be further distinguished as either being APOE ε4 positive or APOE ε4 negative.

Type III APOE ε4 positive produces a defective Apolipoprotein E (ApoE) protein. This defective protein makes it harder for the body to metabolize proteins, fats, and lipids, and it makes it harder for the body to send nutrients and cholesterol to the brain. Thus, APOE ε4 positive patients are hit harder when they develop AD, compared to Type III AD patients that still produce functioning APOE (APOE ε4 negative).

Appropriate therapies may depend on the characterization of AD a patient has. All types will benefit from a combination of an antibiotic such as tetracycline with an immunosuppressant such as sirolimus. Patients with Type III that are APOE ε4 positive should also receive a lipophilic statin such as Atovar (Atorvastatin), which crosses the blood brain barrier.

A dose may take the form of a unit dose. That is, a unit dose is a pill, a tablet or a capsule—one and only one.

For an adult, an appropriate therapy may be one of the following: (a) 50 mg tetracycline, 1 mg sirolimus, 10 mg atorvastatin; (b) 50 mg tetracycline, 1 mg sirolimus, 20 mg atorvastatin; (c) 100 mg tetracycline, 1 mg sirolimus, 40 mg atorvastatin; (d) 100 mg minocycline, 1 mg sirolimus, 80 mg atorvastatin; (e) 50 mg tetracycline, 2 mg sirolimus, 10 mg atorvastatin; (f) 50 mg tetracycline, 2 mg sirolimus, 20 mg atorvastatin; (g) 100 mg tetracycline, 2 mg sirolimus, 40 mg atorvastatin; (h) 100 mg minocycline, 2 mg sirolimus, 80 mg atorvastatin; (i) 2 mg sirolimus 100 mg minocycline and 20 mg atorvastatin. Note, dosages of atorvastatin may be given twice during the day for example to achieve a 20 mg dose a patient may take 10 mg atorvastatin in the morning and 10 mg atorvastatin at another time. The tetracyclines listed above may be either minocycline or doxycycline. Other oral or intravenous tetracyclines may also be used. Simvastatin and Lovastatin which are both lipophilic may also be used.

Doctors prescribing this three-drug approach should be aware of statin effects on cholesterol and triglyceride levels in the patient. In instances where atorvastatin should not be used, atorvastatin may be swapped out for another statin listed above. The dosage of the new statin may be either the same as atorvastatin or adjusted based on the effects of the statin. For patients with high cholesterol or heart disease, the dosage of statin or atorvastatin may be further adjusted slightly to account for a patient's blood chemistry and neurological effects.

If a three drug medication is manufactured including minocycline or doxycycline, sirolimus and atorvastatin, different medications with different atorvastatin dosages may need to be manufactured and distributed to patients with certain diseases. For example, if a pill containing the three drugs is made, one pill for the majority of the population affected with AD may contain 50 mg minocycline, 1 mg sirolimus and 40 mg atorvastatin, but for patients already suffering from high cholesterol and AD, another pill containing 50 mg minocycline, 1 mg sirolimus, and 80 mg atorvastatin may needed. In other instances, for patients already taking a separate dose of atorvastatin or another statin a lower atorvastatin dosed pill may be produced such as 50 mg minocycline, 1 mg sirolimus, and 20 mg atorvastatin.

Effectiveness of the therapy described herein may be apparent in as little as 72 hours. Other times effectiveness may be seen in three to twelve months. Once treatment is effective, the patient may discontinue the therapy under controlled observation for relapse and possible retreatment or continue on a maintenance dose. For AD patients, effectiveness may be measured by the Alzheimer's Disease Assessment Scale-Cognitive (ADAS-Cog) subscale and the Alzheimer's Disease Cooperative Study-Activities of Daily Life (ADCS-ADL) scale or the Mini-Mental Status Examination (MMSE). Both of these tests have been developed over many years, and it is expected that they will continue to be refined.

How often the medications are taken may be varied, as may the time of day. Every day or every other day may be sufficient for some patients, or three days on and two days off. These are examples of drug holidays. Dosage may be different day-to-day. Time of day for taking the medication may be selected based upon the patient having an empty stomach for better absorption.

Drugs in the therapy may be administered together, separately, or at least one separately and at least some together. Drugs in the therapy may be administered orally (e.g. tablets), topically (e.g. patches), intranasally (e.g. inhalation) or parenterally such as by immediate acting formulation or by sustained release formulations, half-life extended injectable formulations, or at least one sustained release formulation, and at least one half-life extended injectable formulation.

The dosage levels may be varied, with daily dosages of doxycycline as low as 40 mg, minocycline as low as 25 mg, and sirolimus as low as 0.5 mg. On the upper end the dosages may be as much as 400 mg (e.g., 200 mg twice per day) of doxycycline, 300 mg (e.g., 150 mg twice per day) of minocycline, and 4 mg (e.g., 2 mg twice per day) of sirolimus. The dosages specified above are for an average adult, and dosage may be correlated to body weight, with heavier patients receiving a larger dose and lighter patients receiving a smaller dose. Dosages need not be correlated to age. Dosages may be slow release.

Progressive dose escalation may be utilized with tetracyclines, immunosuppressants, and statins. Progressive dose escalation may be used either to make the therapy more potent or alleviate adverse side effects caused by the drugs, or cause the side effects to appear later in the treatment thus reducing patient discomfort. Treatments listed may be modified by progressive dose escalation. Progressive dose escalation may be across days or weeks, such as 25% of the full dosage on the first day or week, 50% the second, 75% the third, and 100% thereafter. Other progressive dose escalations may take the form of 50% dosage for an initial period then 100% later.

Other antibiotics that inhibit protein gene transcription, translation and synthesis may be used. Tetracyclines used may either be synthetic, semisynthetic, or naturally occurring. Additionally, if more synthetic tetracyclines are invented in the future, those tetracyclines would likely be useful as well because of the common basic structure of all tetracyclines. The following list of tetracyclines may be used: chlortetracycline, oxytetracycline, demeclocycline, lymecycline, meclocycline, methacycline, minocycline, rolitetracycline, glycecyclines, tigecycline, omadacycline, sarecycline, and eravacycline.

Other immunosuppressants may be used that block B cell function and synthesis of amyloid beta and $PrP^{sc}$, such as are cyclosporin, tacrolimus and everolimus. Macrolides may also be used. Appropriate macrolides include, azithromycin, clarithromycin, erythromycin, fidaxomicin, telithromycin. Other immunosuppressants may also be used including Corticosteroids, Janus kinase inhibitors, calcineurin inhibitors mTOR inhibitors, IMDH inhibitors, biologics, and monoclonal antibodies.

Statins may be used for patients that have Type III and are APOE ε4 positive. Appropriate statins include atovar, atorvastatin, cerivastatin, fluvastatin, lovastatin, mevastatin, pitavastatin, pravastatin, fenofibric acid, alirocumab, etravirine, cyproterone, posaconazole, ticagrelor, bezafibrate, coenzyme Q-10 colesevelam, rosuvastatin, simvastatin, simvastatin+ezetimibe, lovastatin+niacin extended-release, atorvastatin+amlodipine, and simvastatin+niacin extended-release.

A three drug approach may be necessary for certain patients undergoing AD therapy. Patients may require a therapy consisting of minocycline, sirolimus, and atorvastatin. Atorvastatin is also known as Lipitor®. The dosage of atorvastatin can range from 1 mg-100 mg. An appropriate dosage may include 50 mg minocycline, 1 mg sirolimus, and 10 mg atorvastatin. In the event atorvastatin is not used and another statin must be used, the range of other statin may be 0.01 mg-200 mg. For example, if cerivastatin is used an appropriate dosage would be severely less, such as 0.8 mg cerivastatin, 50 mg minocycline, and 1 mg sirolimus.

Despite the failure of BACE inhibitors in treating AD, the amyloid protein deposition hypothesis is valid. These studies failed because the inhibitors acted downstream in the metabolism of amyloid protein. The therapies described herein work at the level of DNA transcription to RNA and RNA transport to the mitochondrion for protein synthesis by binding to the 30S and 50S subunits of the RNA to block amyloid protein synthesis. Plus, normal cellular catabolism eliminates already deposited amyloid beta protein.

Combination therapies for AD work. In trials conducted by medical doctors, patients undergoing the three drug combination therapy have achieved unexpected results. Treatment of several patients, including two identified as Patient A and Patient B herein, with a combination of appropriate dosages and selections of an antibiotic, an immunosuppressant and a statin demonstrated surprisingly good results. The fact that the treatment worked at all, despite prior failures of others and abundant doubt in the field, would not have been expected, and the fact that it worked so quickly was a delightful and unexpected benefit.

Patient A is a 54 year old $APO_{E4}$ positive E3/E4 male who suffered from AD for five years prior to treatment. Patient A had trouble forming complete sentences and required the aid of a chart with pictures to communicate. For basic functions such as eating or going to the bathroom the patient would have to make hand gestures or point to pictures demonstrating activities on a chart. Patient A showed extreme signs of frustration, and on occasions acted out when caregivers could not understand him. Patient A also had trouble completing simple tasks. Patient A could not tie his own shoes and often fumbled several times with doorknobs when trying to open a door. The word recall test adapted from the Alzheimer's Disease Assessment Scale was performed prior to treatment. The patient could not remember or communicate any words from the test.

Patient A was treated with 2 mg sirolimus and 100 mg minocycline and 20 mg atorvastatin once a day for four months. Patient A experienced recovery of speech and could form short phrases and sometimes complete entire sentences. Patient A's use of a picture chart increased, and he became less frustrated and acted out to caregivers less. Patient A experienced resolved aphasia, improved short term memory and improved long term memory. The word recall test adapted from the Alzheimer's Disease Assessment Scale was performed and the patient could remember up to five words.

Patient B is a 65 year old $APO_{E4}$ positive male suffering from AD. Patient B had trouble with everyday tasks such as getting dressed, remembering to eat meals, communicating with caregivers, and remembering his family members. Often times when buttoning his shirt, he would forget to button buttons or misalign buttons. He would forget articles of clothing such as socks or undergarments and had trouble putting on shoes. A caregiver would have to prepare meals and remind Patient B to eat them. Patient B also had difficulty remembering why caregivers were in his home and would inquire as to their identity constantly. Patient B could remember and engage in conversation with his children, but midway through conversations would often ask his children who they were as if they were strangers. The word recall test adapted from the Alzheimer's Disease Assessment Scale was performed prior to treatment. Patient B was able to remember one word each of the three times the test was administered.

Patient B was treated with 2 mg sirolimus 100 mg minocycline and 20 mg atorvastatin once a day for two months. Patient B experienced improvements to short term memory and improvements to long term memory. Patient B stopped missing buttons and could dress himself perfectly. Patient B did not forget meals his caregivers prepared for him. The inquiry into who his children and caregivers were occurred with less frequency. When the word recall test adapted from the Alzheimer's Disease Assessment Scale was performed after treatment Patient B could recall up to 4 words.

Researchers have failed to successfully treat AD because they have failed to understand how the disease's pathophysiology and how it works, and that a single drug will not be sufficient to treat the disease. This is why researchers using tetracyclines alone, or statins alone, to treat AD have been unsuccessful.

Closing Comments

Alzheimer's Disease is a complex disease that presents several druggable targets including a. Intracerebral amyloidosis, b. systemic amyloidosis, c. $APO_{E4}$ and lipid dysmetabolism in astrocytes and microglia in CNS, d. cerebral neuroinflammation, f. systemic inflammation by Tumor Necrosis Factor alpha and Interleukin 1 b and IL 6. These targets call for combination drug therapy. At the simplest AD Therapy can be simplified to two-Drug therapy for $APO_{E4}$ Negative (E2/E3) AD and three-Drug Therapy for $APO_{E4}$ positive AD.

Throughout this description, the embodiments and examples shown should be considered as exemplars, rather than limitations on the apparatus and procedures disclosed or claimed. Although many of the examples presented herein involve specific combinations of method acts or system elements, it should be understood that those acts and those elements may be combined in other ways to accomplish the same objectives. With regard to flowcharts, additional and fewer steps may be taken, and the steps as shown may be combined or further refined to achieve the methods described herein. Acts, elements and features discussed only in connection with one embodiment are not intended to be excluded from a similar role in other embodiments.

As used herein, "plurality" means two or more. As used herein, a "set" of items may include one or more of such items. As used herein, whether in the written description or the claims, the terms "comprising", "including", "carrying", "having", "containing", "involving", and the like are to be understood to be open-ended, i.e., to mean including but not limited to. Only the transitional phrases "consisting of" and "consisting essentially of", respectively, are closed or semi-closed transitional phrases with respect to claims. Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. As used herein, "and/or" means that the listed items are alternatives, but the alternatives also include any combination of the listed items.

It is claimed:

1. A pharmaceutical composition consisting of: an antibiotic or a pharmaceutically acceptable salt thereof, wherein the antibiotic comprises 100 mg of minocycline; an immunosuppressive or a pharmaceutically acceptable salt thereof, wherein the immunosuppressive comprises 2 mg of sirolimus; a statin or a pharmaceutically acceptable salt thereof, wherein the statin consists of 20 mg atorvastatin; and one or more pharmaceutically acceptable carriers, diluents, or excipients.

2. A method of treating an individual having Alzheimer's disease comprising administering to the individual an effective amount of a medication consisting of: an antibiotic or a pharmaceutically acceptable salt thereof, wherein the antibiotic comprises 100 mg of minocycline; an immunosuppressive or a pharmaceutically acceptable salt thereof, wherein the immunosuppressive comprises 2 mg of sirolimus; a statin or a pharmaceutically acceptable salt thereof, wherein the statin consists of 20 mg atorvastatin; and one or more pharmaceutically acceptable carriers, diluents, or excipients.

* * * * *